United States Patent [19]

Eilingsfeld et al.

[11] 3,978,096

[45] Aug. 31, 1976

[54] PRODUCTION OF 1-CHLOROANTHRAQUINONE

[75] Inventors: Heinz Eilingsfeld, Frankenthal; Manfred Patsch, Ludwigshafen, both of Germany

[73] Assignee: BASF Aktiengesellschaft, Ludwigshafen (Rhine), Germany

[22] Filed: June 5, 1974

[21] Appl. No.: 476,398

[30] Foreign Application Priority Data

July 7, 1973 Germany.............................. 2329036

[52] U.S. Cl. ................................................. 260/384
[51] Int. Cl.² ..................... C07C 49/68; C09B 1/00; C09B 1/10
[58] Field of Search .................................... 260/384

[56] References Cited

OTHER PUBLICATIONS

Houben–Weyl, "Methoden Der Organischen Chemie," 8, pp. 489 and 494.

*Primary Examiner*—Paul F. Shaver
*Attorney, Agent, or Firm*—Johnston, Keil, Thompson & Shurtleff

[57] ABSTRACT

1-Chloroanthraquinone is produced by decarboxylation of 4-chloroanthraquinone-1-carboxylic acid in the presence of a carboxamide. The product is a starting material for the production of dyes, pest control agents and pigments.

11 Claims, No Drawings

PRODUCTION OF 1-CHLOROANTHRAQUINONE

The invention relates to a process for the production of 1-chloroanthraquinone by decarboxylation of 4-chloroanthraquinone-1-carboxylic acid in the presence of a carboxamide.

It is known that highly condensed aromatic carboxylic acids can be decarboxylated by heating in quinoline in the presence of copper powder and copper chromite at temperatures of from 230° to 250°C (Houben-Weyl, "Methoden der Organischen Chemie", vol. 8, pg. 489). Simple aromatic carboxylic acids cannot be decarboxylated in this way; only pyrogenic decomposition of the salts of these carboxylic acids leads to this result, as described on page 494.

The decarboxylation of 4-chloroanthraquinone-1-carboxylic acid has not hitherto been described.

It is an object of this invention to provide a novel process for producing 1-chloroanthraquinone in a simple and economical way in good yield and purity.

We have found that 1-chloroanthraquinone is obtained advantageously by the decarboxylation of 4-chloroanthraquinone-1-carboxylic acid in the presence of a carboxamide bearing two substituents on the nitrogen atom at elevated temperature.

The reaction is represented by the following equation:

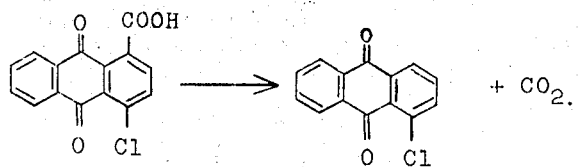 + $CO_2$

It is surprising having regard to prior art methods that the process according to the invention should give 1-chloroanthraquinone in good purity and yield in a simple and economical way. The process also has these advantageous results when a heavy metal catalyst such as a copper compound is used. Under the said conditions, which are similar to those of an Ullmann reaction, the formation of considerable amounts of condensation products or an entirely different reaction would have been expected. It is not necessary to add a base such as quinoline or to use the high reaction temperatures hitherto used.

The reaction of the starting 4-chloroanthraquinone-1-carboxylic acid is carried out as a rule at a temperature of from 100° to 180°C and preferably fron 130° to 160°C at atmospheric or superatmospheric pressure, continuously or batchwise. The carboxamide is conveniently used in an amount of from 2 to 160 moles and preferably from 10 to 30 moles for each mole of starting material.

The carboxamide used may be an aromatic, araliphatic, cycloaliphatic or particularly an aliphatic or cyclic carboxamide. Preferred amides are those of the formula (I):

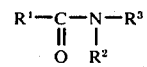 (I)

in which the individual radicals $R^1$, $R^2$ and $R^3$ are identical or different and each is alkyl of one to four carbon atoms, cyclohexyl, aralkyl of seven to twelve carbon atoms or phenyl, the radicals $R^1$ and $R^3$ together with the adjacent carbon atoms and nitrogen atom may be members of a five-membered or six-membered heterocyclic ring or $R^3$ and $R^2$ and the nitrogen atom adjacent to both may be members of a five-membered or six-membered heterocyclic ring, or $R^1$ may also be the radical

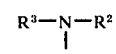

in which $R^2$ and $R^3$ have the above meanings or hydrogen. The radicals and rings may also bear groups which are inert under the reaction conditions, for example alkyl of one to three carbon atoms, as substituents.

Examples of suitable amides (I) are: N,N-dimethylbenzamide, N,N-dimethylformamide, N,N-dimethylacetamide, N,N-dimethylphenylacetamide, N,N-dimethylcyclohexanecarboxamide, N,N-dimethylpropionamide and homologous carboxylic acid piperidides and pyrrolidides; corresponding N,N-diethyl, N,N-diisopropyl, N,N-dibenzyl, N,N-diphenyl, N-methyl-N-phenyl, N-cyclohexyl-N-methyl and N-ehtyl-N-tertbutyl compounds; N-ethylpiperidone-(6), tetramethylurea and appropriate mixtures. Dimethylformamide, diethylformamide, dimethylacetamide, diethylacetamide and N-methylpyrrolidone are preferred. It is convenient to use the carboxamide or one of the carboxamides if necessary in the form of a melt as the liquid reaction medium.

It is advantageous to carry out the decarboxylation in the presence of a heavy metal catalyst which as a rule contains the heavy metal in the form of a compound. Heavy metals of groups Ib, IVb or VIIIb of the Periodic Table are preferred, conveniently titanium, zirconium, iron, cobalt or nickel and particularly copper and thorium. (Groups according to D'Ans-Lax, Taschenbuch fuer Chemiker und Physiker (Springer, Berlin/Heidelberg 1967), page 63.) Examples of heavy metal compounds which may be used are in general the oxides, hydroxides and salts, for example carbonates, bicarbonates, chlorides or nitrates and those compounds which react to form the corresponding oxides during the production of the catalyst or during the reaction. Examples of suitable heavy metal compounds are thorium carbonate, copper nitrate, copper bicarbonate, iron oxalate, nickel formate, copper acetate, copper hydrogen tartrate, cobalt acetate, titanium dioxide, copper(I) oxide, copper(II) oxide, thorium oxide, iron-(III) oxide, nickel oxide, cobalt oxide, and zirconium oxide. Suitable amounts are from 0.1 to 10 and preferably from 1 to 3 gram atoms of heavy metal in the form of a compound based on 1 mole of starting material. The catalysts may if desired be used together with a carrier material, for example pumice, titanium dioxide, steatite, silicon carbide, iron oxides, silicates, for example sodium aluminum silicate, calcium aluminum silicate, bleaching earth, fuller's earth, clays, kaolin, allophanes, zeolites, montmorillonite, Florida earth, quartz, asbestos, mullite, bentonite; silicic acid, silica gel, diatomaceous earth; α-aluminum and γ-aluminum oxides and hydroxides, for example corundum, γ-aluminas, hydrargillite, boehmite, bauxite; aluminum silicates, for example andalusite; titanium dioxide, zirconium dioxide, tin dioxide, magnesite, activated carbon, zinc oxide; alkaline earth metal sulfates or phosphates, for example the calcium or barium salts; metal oxides which upon being calcined with a boron compound form the corresponding borates, for example aluminum oxide, zinc oxide, copper oxide, calcium oxide; or appropriate mixtures of the said carrier materials. The catalyst is conveniently applied to the carrier in an amount of from 1 to 50% by weight based on the carrier.

Organic compounds (chelating agents) which form complex compounds of a higher order, for example internal complex salts, with metals, preferably the abovementioned heavy metals, may be used if desired. Ullmanns Encyklopaedie der technischen Chemie, vol. 10, pgs. 616 et seq. may be referred to for a definition of complex compounds. For example the following compounds are suitable as chelating agents: o-phenanthroline hydrochloride, α-pyridil, alkali metal oxalates, ethylenediamine, benzoin, dithizone, diphenylcarbazone, alkali metal dithiocarbamates, o,o'-dioxyazobenzene; polyamines such as diethylenetriamine, triethylenetetramine, pentaethylenehexamine; complexons such as nitrilotriacetic acid, ethylenediaminetetraacetic acid; α-aminoacids such as serine and glycine; α-hydroxyacids such as tartaric acid; diketones such as acetylacetone and benzoylacetone; oximes such as cupferron and dimethylglyoxime; or appropriate mixtures. From 0.01 to 1 and preferably from 0.02 to 0.1 mole of chelating agent may be used for each mole of starting material.

The reaction may be carried out as follows. A mixture of starting material and carboxamide, conveniently with a heavy metal catalyst and if desired on a carrier and/or with a chelating agent, is kept for from one hour to eight hours at the reaction temperature. The end product is then separated from the reaction mixture by a conventional method, for example by dissolving the mixture in sulfuric acid, precipitating the end product with water and filtering it off.

1-chloroanthraquinone which can be prepared according to the process of the invention is a valuable starting material for the production of dyes, pest control agents and pigments. Ullmanns Encyklopaedie der technischen Chemie, vol. 3, pgs, 674 et seq. may be referred to regarding used for the product.

The following Examples, in which the parts mentioned are parts by weight, will illustrate the process of the invention.

EXAMPLE 1

A mixture of 25 parts of 4-chloroanthraquinone-1-carboxylic acid, 180 parts of N-methylpyrrolidone, 4 parts of copper(I) oxide and 3 parts of o-phenanthroline hydrochloride is heated for two hours at 150°C. The mixture is poured onto ice and the precipitate formed is suction filtered. After the filter cake has been dissolved in 100 parts of concentrated sulfuric acid and reprecipitated with 300 parts of water, filtered and dried in vacuo at 80°C there are isolated 19 parts (90.5% of theory) of 1-chloroanthraquinone having a melting point of 156° to 158°C.

EXAMPLE 2

A mixture of 20 parts of 4-chloroanthraquinone-1-carboxylic acid, 200 parts of dimethylformamide and 3 parts of copper (I) oxide is heated for four hours at 150°C. The end product is precipitated by pouring the mixture into 400 parts of water and filtered. 14 parts (83.4% of theory) of 1-chloroanthraquinone is obtained having a melting point of 154° to 157°C.

EXAMPLE 3

20 parts of 4-chloroanthraquinione-1-carboxylic acid and 15 parts of a catalyst consisting of 20% by weight of throium oxide on silica gel are heated in 200 parts of N-methylpyrrolidone for four hours at 160°C. The mixture is decanted off from the catalyst and the end product is precipitated with 400 parts of water, suction filtered and dried. 12 parts (71.5% of theory) of 1-chloroanthraquinone is obtained having a melting point of 155° to 157°C.

EXAMPLE 4

A mixture of 20 parts of 4-chloroanthraquinone-1-carboxylic acid, 200 parts of N-methylpyrrolidone, 0.5 part of phenanthroline hydrochloride and 10 parts of a catalyst consisting of 20% by weight of copper(I) oxide on silica gel is heated for three hours at 150°C. The catalyst is filtered off and the filtrate is diluted with 400 parts of water. After the mixture has been suction filtered and the filer cake has been dried 14 parts (82.5% of theory) of 1-chloroanthraquinone is obtained having a melting point of 153° to 156°C.

We claim:

1. A process for the production of 1-chloroanthraquinone which comprises decarboxylating 4-chloroanthraquinone-1-carboxylic acid at an elevated temperature in the presence of
   a. a heavy metal catalyst containing a heavy metal of Group Ib, IVb or VIIIb of the Periodic Table, and
   b. about 2 to 160 moles for each mole of starting material of an amide of the formula

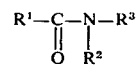

in which:
each of $R^1$, $R^2$ and $R^3$ is alkyl of one to four carbon atoms, cyclohexyl, aralkyl of seven to twelve carbon atoms or phenyl; $R^1$ and $R^3$ when taken together with the adjacent carbon atoms and nitrogen atom complete a five-membered or six-membered heterocyclic ring; $R^2$ and $R^3$ when taken together with the adjacent nitrogen atom complete a five-membered or six-membered heterocyclic ring; or $R^1$ may also be hydrogen or the radical

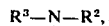

in which $R^2$ and $R^3$ have the above-mentioned meanings; and with the proviso that said amide may bear additional substituents which are inert under the reaction conditions.

2. A process as claimed in claim 1 wherein the reaction is carried out at a temperature of from 100° to 180°C.

3. A process as claimed in claim 1 wherein the reaction is carried out at a temperature of from 130° to 160°C.

4. A process as claimed in claim 1 wherein the reaction is carried out with the carboxamide in an amount of from 10 to 30 moles for each mole of starting material.

5. A process as claimed in claim 1 wherein the reaction is carried out in the presence of an oxide, hydroxide or salt of titanium, zirconium, iron, cobalt, nickel, copper and/or thorium.

6. A process as claimed in claim 1 wherein the reaction is carried out in the presence of a chelating agent.

7. A process as claimed in claim 1 wherein said amide is dimethylformamide.

8. A process as claimed in claim 1 wherein said amide is N-methylpyrrolidone.

9. A process as claimed in claim 5 wherein said amide is dimethylformamide or N-methylpyrrolidone.

10. A process as claimed in claim 9 wherein said calalyst is copper oxide.

11. A process as claimed in claim 9 wherein said catalyst is thorium oxide.

* * * * *